United States Patent [19]
Picha

[11] Patent Number: 6,106,558
[45] Date of Patent: *Aug. 22, 2000

[54] NEURO DECOMPRESSION DEVICE

[75] Inventor: George J. Picha, Independence, Ohio

[73] Assignee: Applied Medical Research, Inc., Garfield Heights, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/929,917

[22] Filed: Sep. 15, 1997

[51] Int. Cl.$^7$ ........................................ A61F 2/02
[52] U.S. Cl. .................................... 623/23.74; 623/17.11; 606/152
[58] Field of Search ............................. 623/8, 11.11, 17, 623/11, 66, 13; 606/76, 152, 23.74; 424/484, 486

[56] References Cited

U.S. PATENT DOCUMENTS

| | | |
|---|---|---|
| 3,176,316 | 4/1965 | Bodell . |
| 4,013,078 | 3/1977 | Feild . |
| 4,187,558 | 2/1980 | Dahlen et al. . |
| 4,255,820 | 3/1981 | Rothermel et al. . |
| 4,877,029 | 10/1989 | Valentini et al. . |
| 4,889,744 | 12/1989 | Quaid .......................................... 623/8 |
| 4,894,063 | 1/1990 | Nashef . |
| 4,955,909 | 9/1990 | Ersek et al. .................................. 623/8 |
| 5,011,486 | 4/1991 | Aebischer et al. ....................... 606/152 |
| 5,019,087 | 5/1991 | Nichols . |
| 5,116,387 | 5/1992 | Berg ......................................... 623/11 |
| 5,147,399 | 9/1992 | Dellon et al. ............................. 623/12 |
| 5,147,404 | 9/1992 | Downey . |
| 5,158,571 | 10/1992 | Picha . |
| 5,207,709 | 5/1993 | Picha ............................................ 623/8 |
| 5,236,453 | 8/1993 | Picha ............................................ 623/8 |
| 5,258,020 | 11/1993 | Ersek et al. ............................... 623/11 |
| 5,271,736 | 12/1993 | Picha . |
| 5,342,628 | 8/1994 | Picha . |
| 5,437,672 | 8/1995 | Alleyne . |
| 5,525,275 | 6/1996 | Iversen et al. ............................... 623/8 |
| 5,674,285 | 10/1997 | Quaid ......................................... 628/8 |
| 5,713,960 | 2/1998 | Christensen et al. ........................ 623/8 |

OTHER PUBLICATIONS

"Spondylolisthesis Treated by a Single–Stage Operation Combining Decompression with in Situ Posterolateral and Anterior Fusion", Michael D. Smith et al., Journal of Bone and Joint Surgery, vol. 72–A, No. 3, pp. 415–421, Mar. 1990.

"Lumbar Spondylolisthesis and Nerve–Root Compression, Operative Experience with 19 Cases Without Spinal Fusion", A. Benin, Neurochirurgia, 23:167, 1980.

"Spinal Cord Injury, Spinal Fracture, and Spinal Stenosis in Aknylosing Spondylitis", Philip R. Weinstein et al., Journal of Neurosurgery, 57:609–616, 1982.

"Mammary Implants: Surface Modifications and the Soft Tissue Response", George J. Picha, M.D., Ph.D., Mammary Implants, vol. 5, No. 2, pp. 54–79, 1991.

"Neurosurgical Manpower: The Physician's Viewpoint", Clark Watts et al., Journal of Neurosurgery, 56:609–614, 1982.

Primary Examiner—Bruce Snow
Attorney, Agent, or Firm—Pearne & Gordon LLP

[57] ABSTRACT

A neuro decompression device is disclosed that significantly reduces fibroplasia proximate to nerve tissue. The device utilizes particular surface topographies to disrupt scar tissue formation around nerves, and which may include one or more drugs to influence tissue growth.

16 Claims, 7 Drawing Sheets

NEURO DECOMPRESSION DEVICE

BACKGROUND OF THE INVENTION

The present invention relates to a device and technique for limiting fibroplasia around nerves, and specifically, proximate the spinal canal, such as may occur after a decompression procedure.

Decompression procedures are performed to release pressure on a nerve trunk by surgically excising constricting bands of tissue or widening a bony canal through which the nerve trunk passes. Details concerning decompression procedures are provided in "Spondylolisthesis Treated by a Single-Stage Operation Combining Decompression with in Situ Posterolateral and Anterior Fusion," Michael D. Smith, Henry H. Bohlman, *Journal of Bone and Joint Surgery*, Vol. 72-A, No. 3, pages 415–421, March 1990; "Lumbar Spondylolisthesis and Nerve-Root Compression, Operative Experience with 19 Cases Without Spinal Fusion," A. Benin; *Neurochirurgia*, 23:167, 1980; and "Spinal Cord Injury, Spinal Fracture, and Spinal Stenosis in Ankylosing Spondylitis," Philip R. Weinstein, Robert R. Karpman, Eric P. Gall, and Michael Pitt, *Journal of Neurosurgery*, 57:609–616, 1982; all of which are herein incorporated by reference.

An unfortunate consequence of such procedures is the formation of scar tissue adjacent the exposed nerve trunk or dura. Scar tissue formation surrounding the dura or nerve trunk tends to contract and calcify, thereby compressing the nerve or spinal cord. Such compression often results in neural complications including for instance, pain in the lower back and hip radiating down the back of the thigh, and dysfunction of the bowel and bladder. Accordingly, there is a need to minimize scar tissue formation around a nerve trunk, and particularly, to limit fibroplasia and recalcification around nerves subsequent to a decompression procedure.

SUMMARY OF THE INVENTION

The present invention achieves the foregoing objectives and provides in a first aspect, a neuro decompression device that is placed proximate to a nerve or region of a nerve. The device has a unique and novel outer surface topography or microstructure that significantly reduces fibroplasia in the vicinity of the device. Preferred surface topographies include a surface characterized by a plurality of depressions, each of the depressions spanning from about 50 microns to about 4000 microns. Another preferred topography provides a plurality of outwardly extending projections having a particular combination of height and width dimensions. Yet another preferred outer surface configuration is one which provides a plurality of fins that are arranged in an offset pattern. All of these surface topographies are described in detail in the accompanying sections below.

In yet another aspect, the present invention provides a method for reducing fibroplasia proximate to a nerve. The method comprises providing a device having one of the unique and novel outer surface topographies described herein and placing the device adjacent to a nerve or region thereof. Fibroplasia in the vicinity of the device and adjacent the nerve is significantly reduced.

In yet another aspect, the present invention provides a neuro decompression device that comprises one or more agents or drugs. The agents or drugs influence tissue growth in and proximate to a nerve and surrounding area.

DESCRIPTION OF THE PREFERRED EMBODIMENTS

The present invention, in a first aspect, provides an implant device for implantation in a mammalian body, preferably a human body. The implant device is placed adjacent to an exposed region of a nerve, such as within a void resulting from removal of bone along a vertebral foramen or along the spinal canal. The implant device comprises a pliable, flexible, or resilient shielding body that utilizes unique surface topographies or microstructures to disrupt and limit the formation of scar tissue, i.e. fibroplasia, about the nerve and thereby inhibit subsequent contracture. In a second aspect, the present invention provides a method for significantly reducing the potential for fibroplasia around a nerve by use of the noted implant device. In other aspects, all of which are described below, the invention provides an implant device comprising one or more agents that influence tissue growth.

The present invention is particularly well suited for reducing fibroplasia around a nerve root, and particularly along a region of a nerve passing through a foramen in a vertebra, sacrum, or other bony member.

Figure 1:
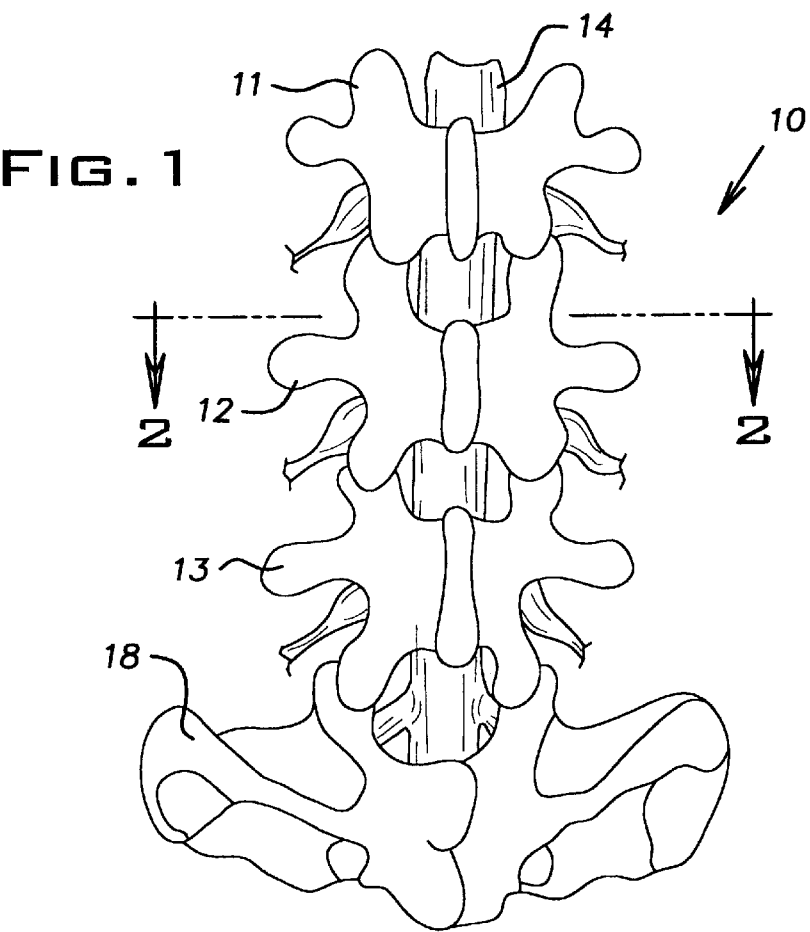
FIG. 1 illustrates a lower portion of a vertebral column and spinal cord.

FIG. 1 illustrates a lower portion of a spinal column 10 comprising a third lumbar vertebra 11, a fourth lumbar vertebra 12, and a fifth lumbar vertebra 13, all descending to the ilium 18, and encasing the spinal cord 14. The spinal cord 14 is disposed within a spinal canal 20. Thoracic vertebrae are disposed immediately above the lumbar vertebrae.

Figure 2:
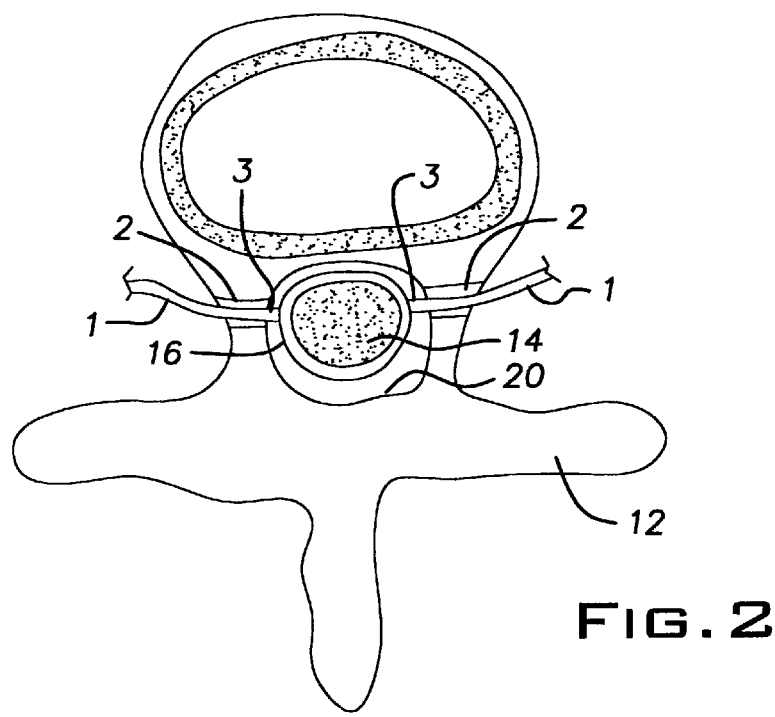
FIG. 2 illustrates a transverse sectional view of a lumbar vertebra in the vertebral column taken along line 2—2 shown in FIG. 1, showing in greater detail passage of a nerve through a vertebral foramen.

FIG. 2 is a transverse sectional view of the lumbar vertebra 12 taken along line 2—2 in FIG. 1. FIG. 2 illustrates passage of a nerve 1 through a foramen 2 defined in the vertebra 12. The nerve 1 is joined to the spinal cord 14 at a nerve root 3.

Figure 3:
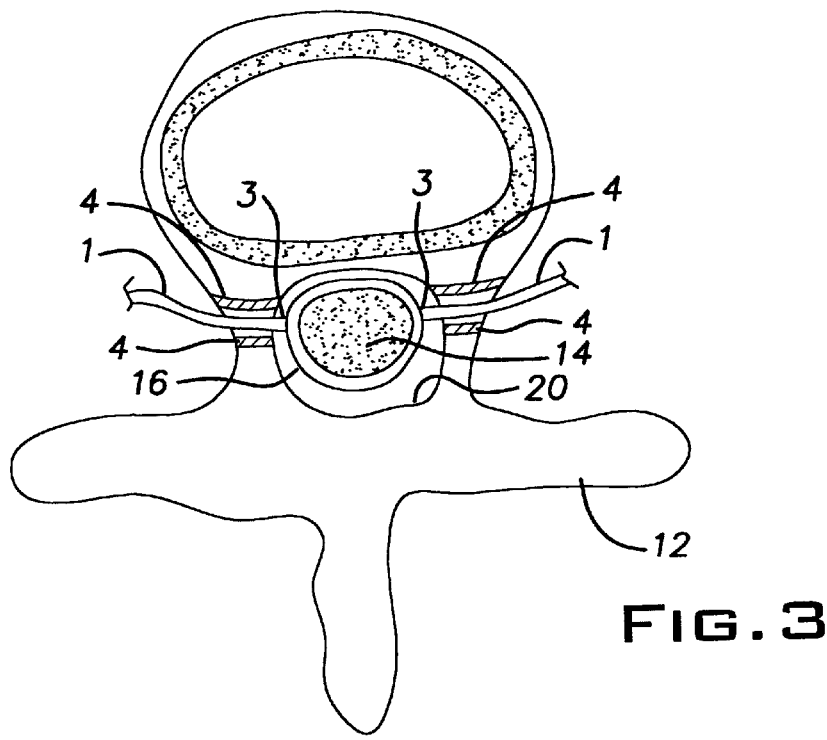
FIG. 3 illustrates the vertebra depicted in FIG. 2 after dissective widening of the vertebral foramen.

As noted, it may be necessary to widen a foramen or bony area surrounding a nerve. FIG. 3 illustrates the vertebra 12 of FIG. 2 after dissective widening of the foramen 2 thereby creating a widened region 4. As will be appreciated, the widened region 4 provides significantly greater clearance between the nerve 1 and nerve root 3, and the bony walls of the vertebra 12 defining the now widened foramen.

Figure 4:
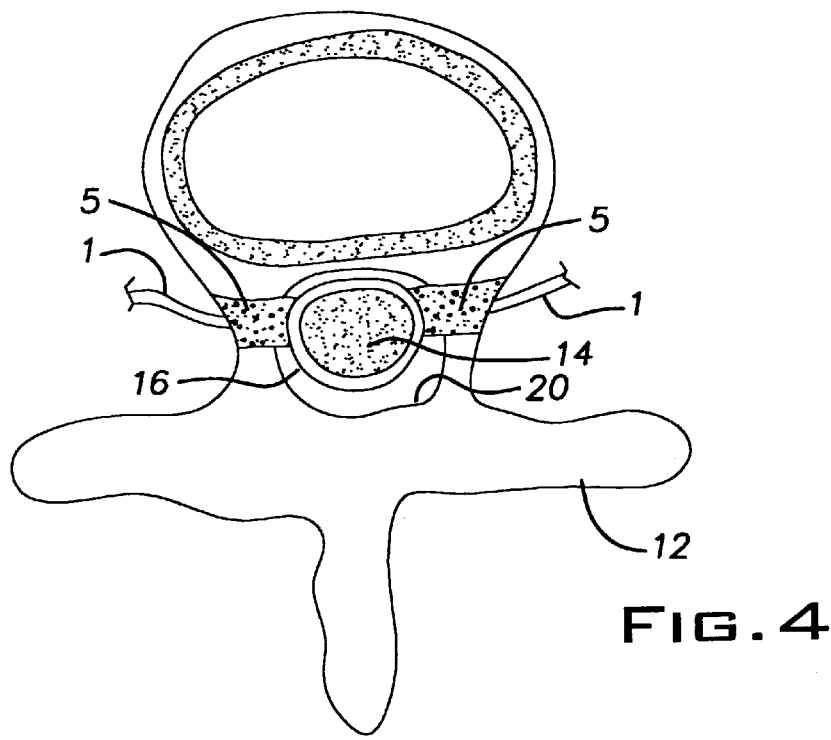
FIG. 4 illustrates the vertebra of FIG. 3 having a neuro decompression device disposed within the widened region.

FIG. 4 illustrates a neuro decompression device 5 in accordance with the present invention disposed in the widened region 4. The neuro decompression device 5 is preferably disposed in intimate contact with the nerve 1 and the nerve root 3. The neuro decompression device 5 preferably has particular topographies or structures. These details and other preferred aspects are described below in conjunction with another neuro decompression device in accordance with the present invention. It will be understood that all of the aspects and details set forth below apply to the previously noted device 5.

As noted, the present invention neuro decompression device is also well suited for placement within a dissection region along the spinal cord.

Figure 5:
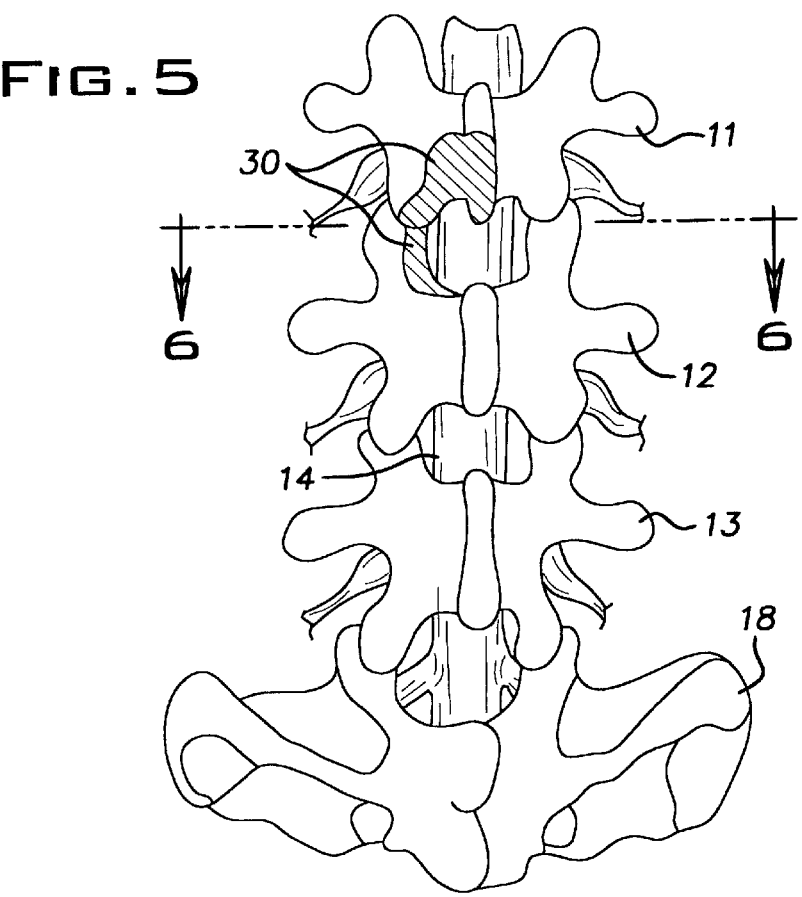
FIG. 5 illustrates bony dissection of adjacent lumbar vertebra in the vertebral column depicted in FIG. 1.

FIG. 5 illustrates a dissection region 30 extending over adjacent portions of the third lumbar vertebra 11 and the fourth lumbar vertebra 12, and exposing the spinal cord 14.

Figure 6:
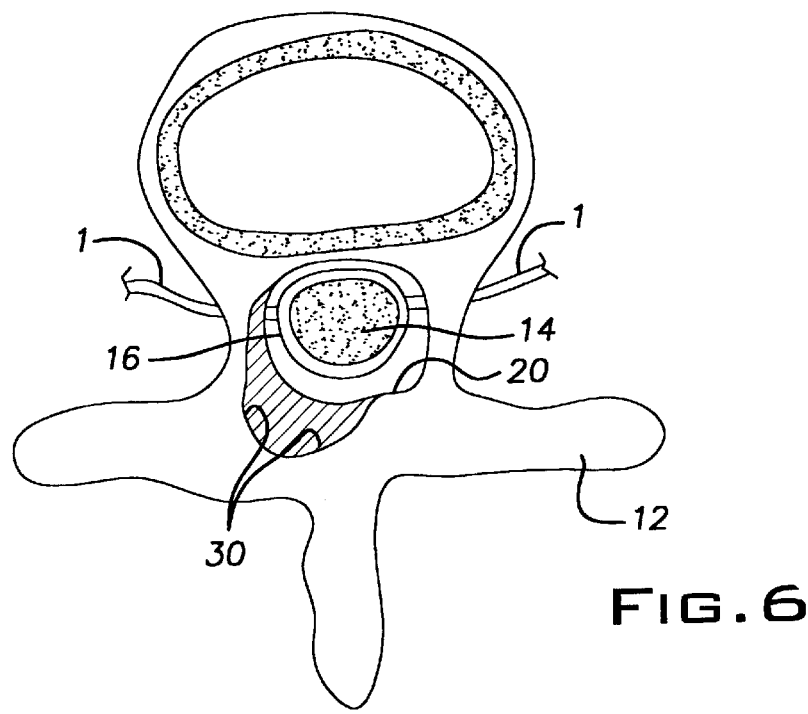
FIG. 6 is a cross-section of the spinal column taken over line B—B in FIG. 5, illustrating a dissected lumbar vertebra.
Figure 7:
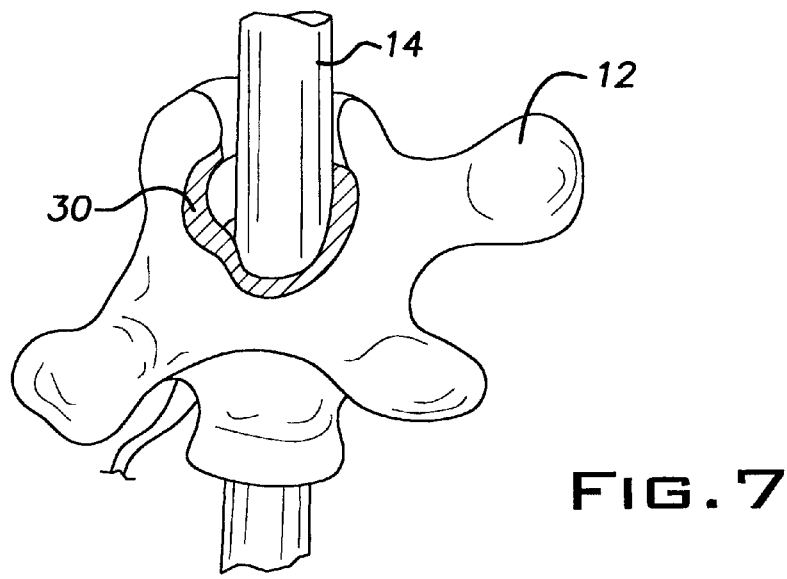
FIG. 7 illustrates in greater detail the dissected lumbar vertebra and exposed spinal cord of FIG. 6.

FIGS. 6 and 7 illustrate in greater detail the dissection region 30 providing access to the spinal cord 14 and surrounding dura 16 disposed within a spinal canal 20.

Figure 8:
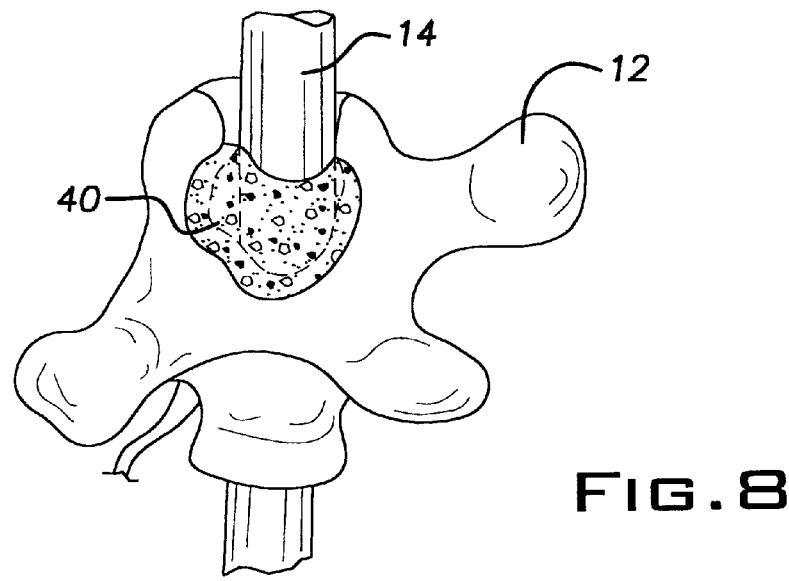
FIG. 8 illustrates the vertebra depicted in FIG. 7 having a first preferred embodiment neuro decompression device disposed within the dissection region.
Figure 9:
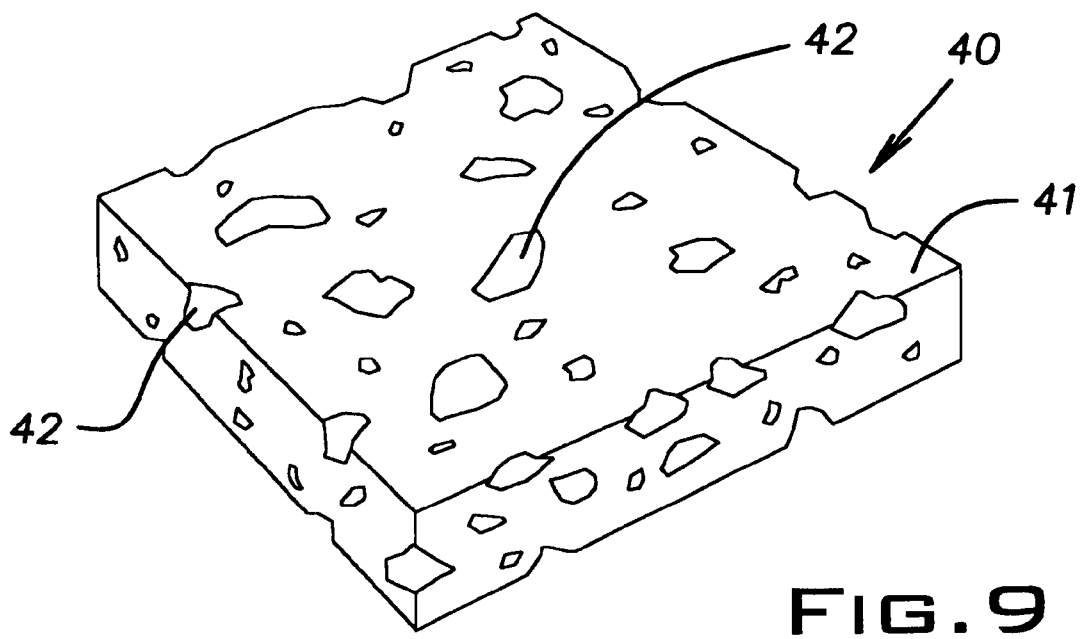
FIG. 9 is a detailed view of the surface of the first preferred embodiment device depicted in FIG. 8.

FIG. 8 illustrates a first preferred embodiment neuro decompression device 40 disposed within the dissection region 30 and overlying the exposed spinal cord 14 and dura 16. FIG. 9 illustrates in greater detail a portion of the outer surface 41 of the device 40. The outer surface 41 is irregular and defines numerous randomly dispersed depressions 42. The distance across a typical depression, i.e. its "span" as referred to herein, ranges from about 50 microns to about 4000 microns. It is preferred that the spans each range from about 200 microns to about 2500 microns, and more preferably from about 300 microns to about 2000 microns. It is even more preferred that the spans range from about 400 microns to about 1500 microns. It is particularly preferred that the spans range from about 450 microns to about 800 microns, with an average span of approximately 500 microns being most preferred. The shape of the depressions 42 is generally irregular, however most approach a shape that resembles a circle or oval as seen along the outer surface 41. It is preferred that the device 40 also have a cavernous interior structure adjacent the outer surface 41. That is, it is preferred that one or more interior voids or hollow regions are defined within the device 40 proximate to the outer surface 41. It is most preferred that at least some of these interior voids or cavities, particularly those defined proximate to the outer surface 41, be accessible from the exterior of the device through one or more depressions 42. Accordingly, a relatively small depression 42 may provide access to a significantly larger hollow region disposed beneath the outer surface 41. It is also most preferred that at least a portion of the interior voids be interconnected. Although not wishing to be bound to any particular theory, it is believed that the noted cavities serve as transport regions for carrying one or more drugs described herein, or may also serve as receptacles within which may grow tissue.

The device 40 is preferably formed from a foamed material. The material is preferably an open cell foam, and most preferably comprising at least a majority of open cells. The average cell diameter ranges from about 50 microns to about 4000 microns and preferably from about 100 microns to about 3000 microns, however larger or smaller cell sizes can be utilized. Typically, the average cell diameter is about 500 microns. The references for various cell diameters corresponds to the previously noted preferences for span dimensions.

The material for device 40 can be nearly any biocompatible material that can be foamed, including for instance, a polymeric material such as polyurethane or silicone. As used herein, the term polymer also includes homopolymers, copolymers, terpolymers, interpolymers and blends thereof. Illustrative polymers suitable for forming the device 40 include silicones, polystyrenes, polyurethanes, silicone and polystyrene copolymers, polystyrene and butadiene copolymers, and acrylonitrile-butadiene-styrene resins. Representative silicone polymers include medical grade silicone rubbers such as those suitable for implants: diphenylpolysiloxane, dimethylpolysiloxane (dimethicone), phenylmethylpolysiloxane, trifluoropropylmethylsiloxane, copolymers of dimethylpolysiloxane and polymethylmethacrylate and mixtures thereof. Other suitable foamed materials include for example, INTERPORE material. Remarkably, the use of a foamed material for the device 40 significantly disrupts and delays fibroplasia and disorganizes fibrous tissue matrices, and specifically, collagen fibers. Such disruption and disorganization reduces the potential for contracture about the nerve or spinal cord.

Figure 10:
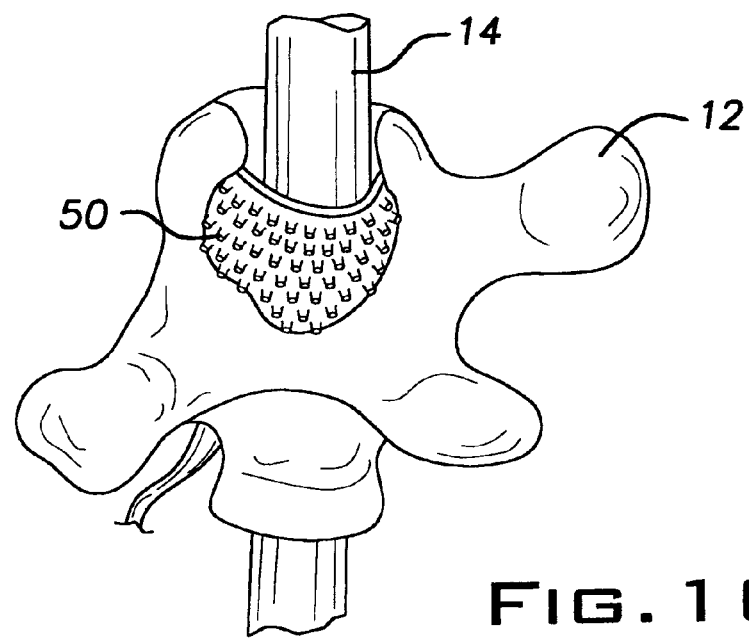
FIG. 10 illustrates the vertebra depicted in FIG. 7 having a second preferred embodiment neuro decompression device disposed within the dissection region.
Figure 11:
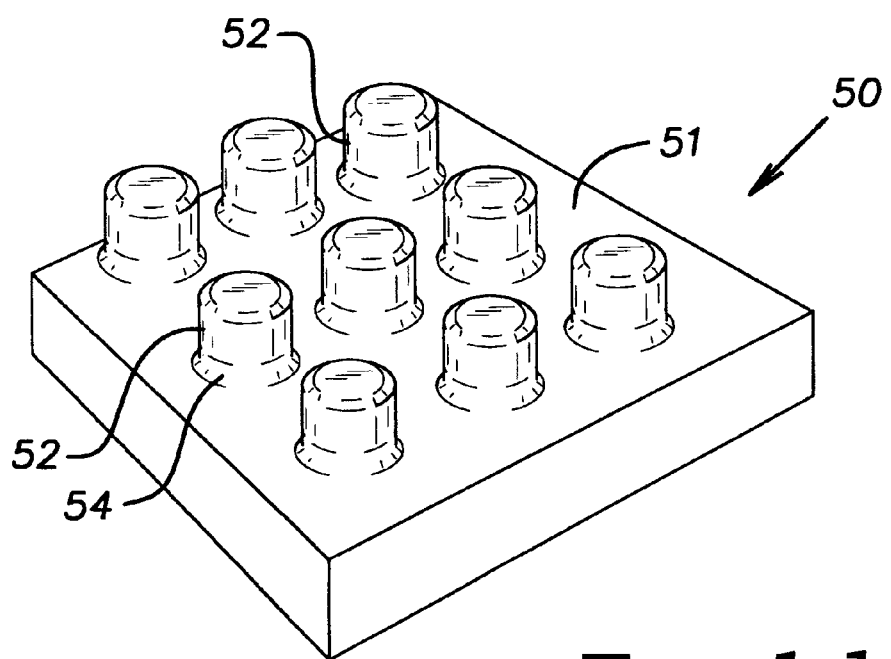
FIG. 11 is a detailed view of the surface of the second preferred embodiment device depicted in FIG. 10.

FIG. 10 illustrates a second preferred embodiment neuro decompression device 50 disposed within the previously described and exemplary dissection region 30. FIG. 11 illustrates in greater detail a region of the outer surface 51 of the device 50. The outer surface 51 is characterized by a plurality of outwardly projecting pillars 52. Outwardly projecting pillars on either or both sides of the neuro decompression device significantly disrupt subsequent fibroplasia. The height of the pillars 52 ranges from about 50 microns to about 5000 microns. It is preferred that the height of the pillars 52 ranges from about 400 microns to about 3,300 microns, and more preferably from about 750 microns to about 1600 microns. More preferably, the height of the pillars 52 is selected in combination with the width of the pillars 52 as set forth below.

The width of the pillars 52 ranges from about 50 microns to about 1000 microns. It is preferred that the width of the pillars 52 ranges from about 100 microns to about 900 microns, and more preferably from about 250 microns to about 800 microns. More preferably, the width of the pillars 52 is selected in combination with the height of the pillars 52 as set forth below.

Preferably, the height and width of the pillars 52 is selected from combinations of dimensions comprising (1) an approximate height of 750 microns and an approximate width of 250 microns and (2) an approximate height of 1600 microns and an approximate width of 800 microns. The pillars 52 are shown in FIG. 11 as circular in cross-section and having a thickened portion or fillet 54 at their base. The thickened portion 54 provides a smooth joint or transition region between the pillars 52 and the outer surface 51 of the device 50. The thickened portion 54 also increases the strength of attachment between the pillars 52 and the outer surface 51. The pillars 52 are generally columnar or rod-like in shape. The pillars 52 may be of a tapered shape or a truncated-cone shape. The pillars 52 are preferably circular in cross-section, but may also be square, rectangular, triangular, rounded, or any other cross-section. Projections of non-circular cross-section should preferably be thickened near the base for the reasons previously described. The top of the pillars 52 may be flat, convex, or concave. As shown in FIG. 11, the pillars 52 are uniformly arranged, however nearly any pattern, including random dispersion, may be utilized. The pillars 52 may extend from the majority of, from substantially all of, or from less than all of the outer surface 51 of the device 50.

The pillars 52 are also spaced apart from one another. The lateral spacing, that is the edge-to-edge distance between adjacent pillars 52, ranges from about 50 microns to about 4000 microns. Preferably, the lateral spacing ranges in relation to the preferred widths of the pillars 52 as follows. For a 250 micron wide pillar, the lateral spacing ranges from about 100 to about 1250 microns. It is further preferred that the lateral spacing ranges from about 200 microns to about 1000 microns, and even more preferred from about 250 microns to about 800 microns. It is most preferred that the lateral spacing be about 250 microns or about 500 microns. In the case of an 800 micron wide pillar, the lateral spacing ranges from about 320 to about 4000 microns. It is preferred that the lateral spacing ranges from about 350 microns to about 2800 microns, and further preferred from about 375 microns to about 1500 microns. It is even more preferred that the lateral spacing ranges from about 400 microns to about 800 microns. More preferably, the lateral spacing is about 400 microns, or about 500 microns, or about 600 microns, or about 700 microns, or about 800 microns. Details of the pillar or columnar surface morphology utilized by the second preferred embodiment neuro decompression device 50 are described in U.S. Pat. No. 5,158,571 to Picha, which is herein incorporated by reference. A significant advantage of utilizing a pillar morphology is that if the neuro decompression device is removed, the pillars are generally not attached to adjacent interconnective tissue, and so, the pillars can be slipped past and from the surrounding tissue.

The implant device 50 and the pillars 52 can be made of any suitable implantable or medical grade material, preferably inert, as known in the art, including for example HP SILASTIC, a high-performance silicone elastomer produced by Dow Corning, and other silicone and polymeric elastomers. The material can also be implantable or medical grade ceramics, metals or polymers. The pillars 52 can be integrally formed with the device 50. For example, the pillars may be formed by molding, by lasers, or by the use of milling or ion-beam milling techniques which are known in the art.

Figure 12:
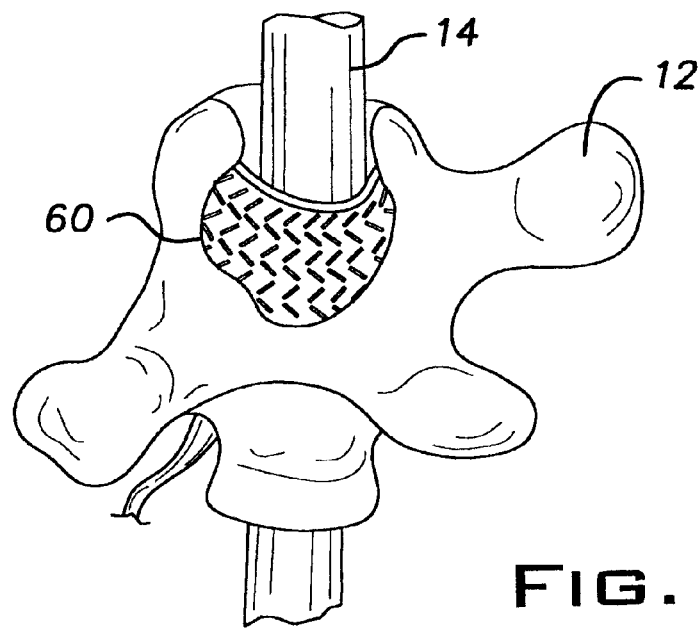
FIG. 12 illustrates the vertebra depicted in FIG. 7 having a third preferred embodiment neuro decompression device disposed within the dissection region.
Figure 13:
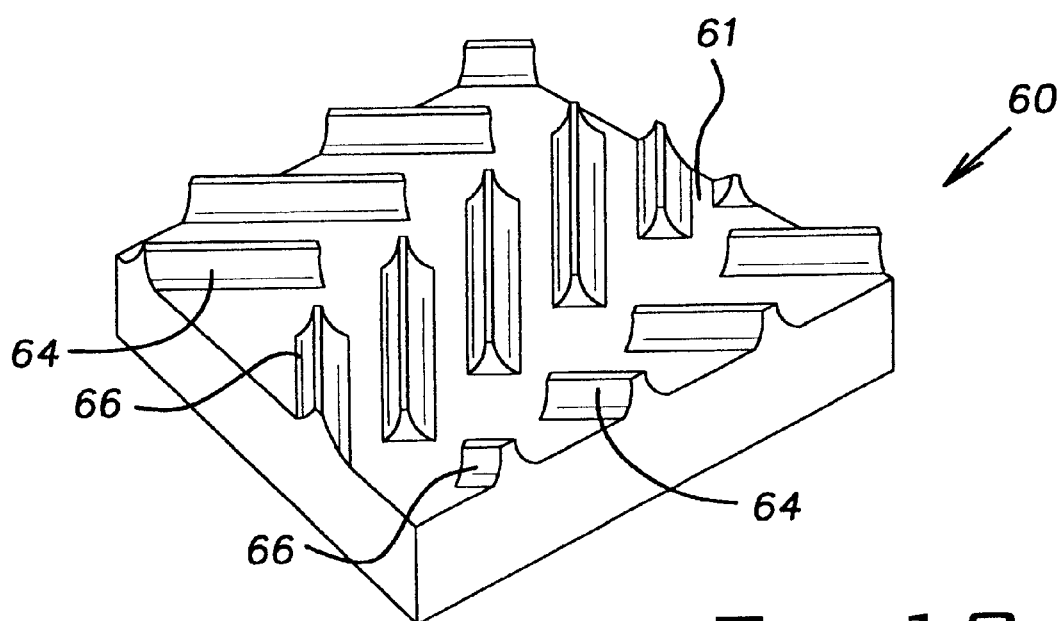
FIG. 13 is a detailed view of the surface of the third preferred embodiment device depicted in FIG. 12.

FIG. 12 illustrates a third preferred embodiment neuro decompression device 60 disposed within the dissection region 30. FIG. 13 illustrates in greater detail a region of the outer surface 61 and a plurality of fins 64 of the device 60. The outer surface 61 is characterized by a plurality of fins 64 that are arranged in an "offset pattern." The term "offset pattern" as used herein refers to an arrangement of fins that form a tortuous or sinuous path between fins along the outer surface 61 of the device 60. In FIG. 13, the fins are arrayed in an offset pattern on the outer surface 61 of the implant device 60. This arrangement disrupts long-range ordering of scar tissue formation adjacent the implant device. As can be seen in FIG. 13, the fins 64 are separate and distinct from each other and unconnected. That is, they stand alone and are not joined with each other to form walls, polygonal structures, etc. The fins 64 may extend over all or less than all of the outer surface 61 of the device 60.

The fins 64 are preferably arrayed in a regular pattern on the outer surface 61 of the implant device 60. However, they may also be arranged in an irregular array, so long as sinuous paths as previously described are formed. Each fin 64 has a length substantially greater than its width. The length is about three times the width or more. This configuration promotes the formation of sinuous paths along the outer surface 61. The ratio of the length of the fin to the width of the fin is from about 3:1 up to about 10:1. This ratio of fin length to fin width is preferably more than 3:1 and most preferably from about 4:1 to about 6:1. Preferably, each fin is about 100 to about 1000 microns wide and most preferably about 200 to about 500 microns wide. Preferably, the spacing between adjacent fins is about the same as the previously noted fin widths.

Preferably the height of the fins 64 is substantially uniform and is between about 200 and about 2500 microns. Most preferably, fin height ranges from about 1000 to about 2000 microns. The sides of the fins need not necessarily be perpendicular with respect to the outer surface 61, nor flat. They may be tapered.

Referring further to FIG. 13, the fins 64 preferably have a thickened portion or fillet 66 at their base. The thickened portion 66 provides a smooth joint or transition region between the fin 64 and the outer surface 61 of the device 60. The thickened portion 66 also increases the strength of the attachment between the fin 64 and the outer surface 61. The top of the fin 64 is shown as flat. It can also be convex or concave or combinations thereof. The ends of the fin 64 can be rounded, flat, or otherwise shaped.

The implant device 60 and the fins 64 can be made of any suitable implantable or medical grade material, preferably inert, as known in the art, including HP SILASTIC, and other silicone and polymeric elastomers. The material can also be implantable or medical grade ceramics, metals or polymers. The fins 64 can be integrally formed with the supporting structure. For example, the fins 64 may be formed by molding, by lasers, or by the use of milling or ion-beam milling techniques which are known in the art. Details of various fins and offset patterns are described in U.S. Pat. No. 5,207,709 to Picha, which is herein incorporated by reference.

Another contemplated surface morphology for the neuro decompression device of the present invention is a McGhan Biocell Surface. This surface and its characteristics is discussed in an article by the inventor of the present invention, "Mammary Implants: Surface Modifications and the Soft Tissue Response," *Mammary Implants,* Vol. 5, No. 2, pages 55, 63–66, 1991, which is hereby incorporated by reference.

It will be understood that the neuro decompression device 5 is schematically depicted in FIG. 4. That is, the device 5 may be in the form of any of the previously described first, second, or third embodiments 40, 50, or 60, respectively, described herein. The device 5 may also utilize the above-noted McGhan Biocell Surface.

In another aspect, the present invention provides a neuro decompression device that administers one or more agents or drugs. Preferably, the neuro decompression device administers a drug to influence tissue growth in and proximate to the dissection region and nerves. Most preferably, a neuro decompression device is impregnated with a drug that inhibits the formation of adhesions.

As used herein, the term "drug" broadly includes physiologically or pharmacologically active substances for producing a localized effect at the administration site or a systemic effect at a site remote from the administration site. Such drugs include inorganic and organic compounds, for example, drugs which act on the central nervous system such as hypnotics and sedatives, psychic energizers, tranquilizers, anticonvulsants, muscle relaxants and anti-parkinson agents, antipyretics and anti-inflammatory agents, local anesthetics, anti-spasmodics and anti-ulcer agents, prostaglandins, antibiotics, hormonal agents, steroids that affect fibroblasts/ fibroblast sites, steroids that affect osteoblasts/osteoblast sites in fibroplasia, estrogenic steroids, progestational steroids, such as for contraceptive purposes, sympathomimetic drugs, cardiovascular drugs, diuretics, antiparasitic agents, hypoglycemic drugs and ophthalmic drugs. The antibiotics are of particular importance and application herein. Illustrative water-soluble antibiotics include, without limitation, cephalothin, neomycin, ampicillin, tobramycin, kanamycin, tetracycline, lincomycin, nitrofurantoin, bacitracin, and nystatin. The drug should be a solid or convertible to solid form by reaction, such as salt formation and crystallization.

As noted, the neuro decompression device preferably administers a drug that influences tissue growth, and most preferably, inhibits the formation of adhesions in and proximate to the dissection region and nerves. Preferred examples of materials suitable for delaying wound healing or generally affecting fibroplasia include, but are not limited to, steroids, chondroitin sulfates, polyvinylpyrrolidone, glycoproteins, mucopolysaccharides, and derivatives thereof. It is also contemplated to use related gel materials, i.e. those materials that exhibit similar effects. It is particularly preferred to utilize one or more of these agents in conjunction with the previously described neuro decompression devices 5, 40, 50, and 60.

The device of the present invention may be provided in a sheet form. It is contemplated that a surgeon or other medical professional may readily trim or otherwise cut the device from a sheet of bulk material to match the configuration of the widened foramen, canal, or dissection region, or at a minimum, to overlay the exposed nerve area. Depending upon the material selected, it is contemplated that the neuro decompression device can be further bent or shaped to match the particular configuration of the placement region. The device may also be rolled in a cuff shape or cylindrical shape and placed about the exterior periphery of the nerves. For instance, any of the devices 5, 40, 50, or 60 could be cut or otherwise severed from a relatively large sheet of material having the particular structure and surface topography characteristics of the device 5, 40, 50, or 60. Alternatively, the device could be pre-shaped or otherwise preformed into one or more patterns for subsequent use. Although not wishing to be bound to any particular size or proportion limitations, the preferred embodiment devices 5, 40, 50, and 60 will generally be rectangular or oblong in shape. Typical lengths range from about 1 to about 3 centimeters. Typical widths range from about 2 millimeters to about 1 centimeter. The overall thickness of the previously noted devices, excluding pillars and fins if utilized, generally ranges from about 1000 microns to about 5000 microns. It will be appreciated that greater or lesser thicknesses may be employed depending upon the application.

The implant devices 5, 40, 50, and 60 of the present invention, may be placed at the desired location within the surgical site by direct surgical placement, or by endoscopic techniques. A particularly preferred technique for placing a foamed device such as the first preferred device 40 within the surgical site is by providing the device 40 in a compressed state, inserting or otherwise placing the device 40 at the desired location, and then allowing the device 40 to expand and thereby occupy the void or open region of the site. In order to maintain the device 40 in a compressed state while it is being inserted, the device 40 may be encapsulated in a water-soluble gelatin. Once the device 40 is at the desired location, the gelatin dissolves and allows the device 40 to expand. Alternately, the device 40 may be wrapped or bound in a water-soluble suture thread or film or other web or thread made of a material which may safely be dissolved at the location. The extent of expansion of the device 40 is tailored such that excessive pressure is not exerted upon the surrounding tissue, and particularly upon the nerve adjacent the device 40.

All of the devices 5, 40, 50, and 60 may be utilized in combination with known gels such as those available from Gliatech of Cleveland, Ohio.

Although the invention has been described in terms of several preferred embodiment implant devices adapted for placement over nerves, it is to be understood that the invention is less preferably applicable to any bodily conduit besides a nerve or nerve root that passes through a duct or passage defined in hard tissue or bone, and which is susceptible to fibroplasia. Other less preferred examples of applications for the present invention include placing implant devices as described herein over exposed regions of the urethra tube or vascular conduits.

While the foregoing details what is felt to be the preferred embodiments of the present invention, no material limitations to the scope of the claimed invention is intended. Further, features and design alternatives that would be obvious to one of ordinary skill in the art are considered to be incorporated herein. The scope of the invention as set forth is particularly described in the claims hereinbelow.

What is claimed is:

1. A neuro decompression device for placement proximate to a nerve disposed in a canal extending through hard tissue or bone, said device comprising a flexible shielding body sized to cover said nerve in said canal, said shielding body being movable between an unflexed state outside of the canal, wherein the shielding body is generally rectangular in shape, and a flexed state inside the canal, wherein the shielding body is rolled in a cuff share and disposed about a periphery of the nerve, said shielding body having an outer surface texturized with outwardly-extending microstructures to reduce fibroplasia in the vicinity of said device, said microstructures having a height of about 50 microns to about 5,000 microns.

2. The neuro decompression device of claim 1, said device further comprising an agent that affects tissue growth.

3. The neuro decompression device of claim 2, wherein said agent is a drug that inhibits the formation of adhesions to said device.

4. The neuro decompression device of claim 3, wherein said drug is selected from the group consisting of steroids, chondroitin sulfates, polyvinylpyrrolidone, glycoproteins, mucopolysaccharides, and combinations thereof.

5. The neuro decompression device of claim 1, wherein said microstructures comprise a plurality of outwardly extending projections, said projections having a combination of dimensions selected from the group consisting of (1) an approximate height of 750 microns and an approximate width of 250 microns, and (2) an approximate height of 1600 microns and an approximate width of 800 microns.

6. The neuro decompression device of claim 5, wherein said 250 micron wide projections are spaced from each other a distance of from about 100 microns to about 1250 microns.

7. The neuro decompression device of claim 5, wherein said 800 micron wide projections are spaced from each other a distance of from about 320 microns to about 4000 microns.

8. The neuro decompression device of claim 5, said device further comprising a drug selected from the group consisting of steroids, chondroitin sulfates, polyvinylpyrrolidone, glycoproteins, mucopolysaccharides, and combinations thereof.

9. The neuro decompression device of claim 1, wherein said microstructures comprise a plurality of fins arranged in an offset pattern.

10. The neuro decompression device of claim 9, wherein each of said fins has a length to width ratio of from about 3:1 to about 10:1.

11. The neuro decompression device of claim 10, wherein said ratio is from about 4:1 to about 6:1.

12. The neuro decompression device of claim 9, wherein each of said fins has a width of from about 100 to about 1000 microns wide.

13. The neuro decompression device of claim 12, wherein said width is between about 200 and about 500 microns.

14. The neuro decompression device of claim 9, wherein each of said fins has a height from about 200 to about 2500 microns.

15. The neuro decompression device of claim 14, wherein said height is between about 1000 and about 2000 microns.

16. The neuro decompression device of claim 9, said device further comprising a drug selected from the group consisting of steroids, chondroitin sulfates, polyvinylpyrrolidone, glycoproteins, mucopolysaccharides, and combinations thereof.

* * * * *

UNITED STATES PATENT AND TRADEMARK OFFICE
CERTIFICATE OF CORRECTION

PATENT NO. : 6,106,558
DATED : August 22, 2000
INVENTOR(S) : Picha

It is certified that error appears in the above-indentified patent and that said Letters Patent is hereby corrected as shown below:

Column 8, line 35, delete "share" and insert --shape--.

Column 8, line 40, after "microns" insert --said microstructures being distributed over a majority of said outer surfaces--.

Signed and Sealed this

Twenty-fourth Day of April, 2001

Attest:

NICHOLAS P. GODICI

Attesting Officer

Acting Director of the United States Patent and Trademark Office